United States Patent [19]

Pratt

[11] Patent Number: 5,026,363

[45] Date of Patent: Jun. 25, 1991

[54] FLUSHABLE DIAPER DEVICE AND METHOD

[75] Inventor: Darin D. Pratt, Montrose, Colo.

[73] Assignee: RMED International, Inc., Delta, Colo.

[21] Appl. No.: 457,336

[22] Filed: Dec. 27, 1989

[51] Int. Cl.⁵ .............................................. A61F 13/00
[52] U.S. Cl. .................................. 604/385.1; 604/366; 604/377
[58] Field of Search .................... 604/375, 365, 385.1, 604/366, 377, 378

[56] References Cited

U.S. PATENT DOCUMENTS

| | | | |
|---|---|---|---|
| 3,658,062 | 4/1972 | Kapur | 604/375 |
| 3,665,923 | 5/1972 | Champaigne | 604/365 |
| 3,699,966 | 10/1972 | Chapuis | 604/377 |
| 4,057,061 | 11/1977 | Ishikawa et al. | 604/377 |
| 4,500,315 | 2/1985 | Pieniak et al. | 604/379 |
| 4,589,877 | 5/1986 | Sivilich | 604/385.1 |
| 4,880,417 | 11/1989 | Yabrov et al. | 604/379 |

Primary Examiner—Stephen C. Pellegrino
Assistant Examiner—Gary Jackson
Attorney, Agent, or Firm—Harry M. Weiss; Antonio R. Durando

[57] ABSTRACT

A diaper primarily for use by a baby or toddler, and also usable by a person as required, is provided. The diaper has a hour glass, bikini bottom shape with front, and center and back portions. The diaper has a multi-layer construction including a first exterior bottom layer and a second middle layer and a third interior top layer. The interior and exterior layers are each about 1 mil in thickness and the middle layer is about several mils in thickness. The interior layer is a thin, moisture permeable biodegradable material. The middle layer is a thin, high moisture absorbing breathable, biodegradable material. The exterior layer is a thin, low density breathable, hydrophobic layer. Thus, this diaper is easily flushable down a toilet. Also, the diaper has separation means which can include a tear string for tearing the exterior layer for separating the diaper into two parts for flushing separate pieces thereof together in a single flush.

13 Claims, 3 Drawing Sheets

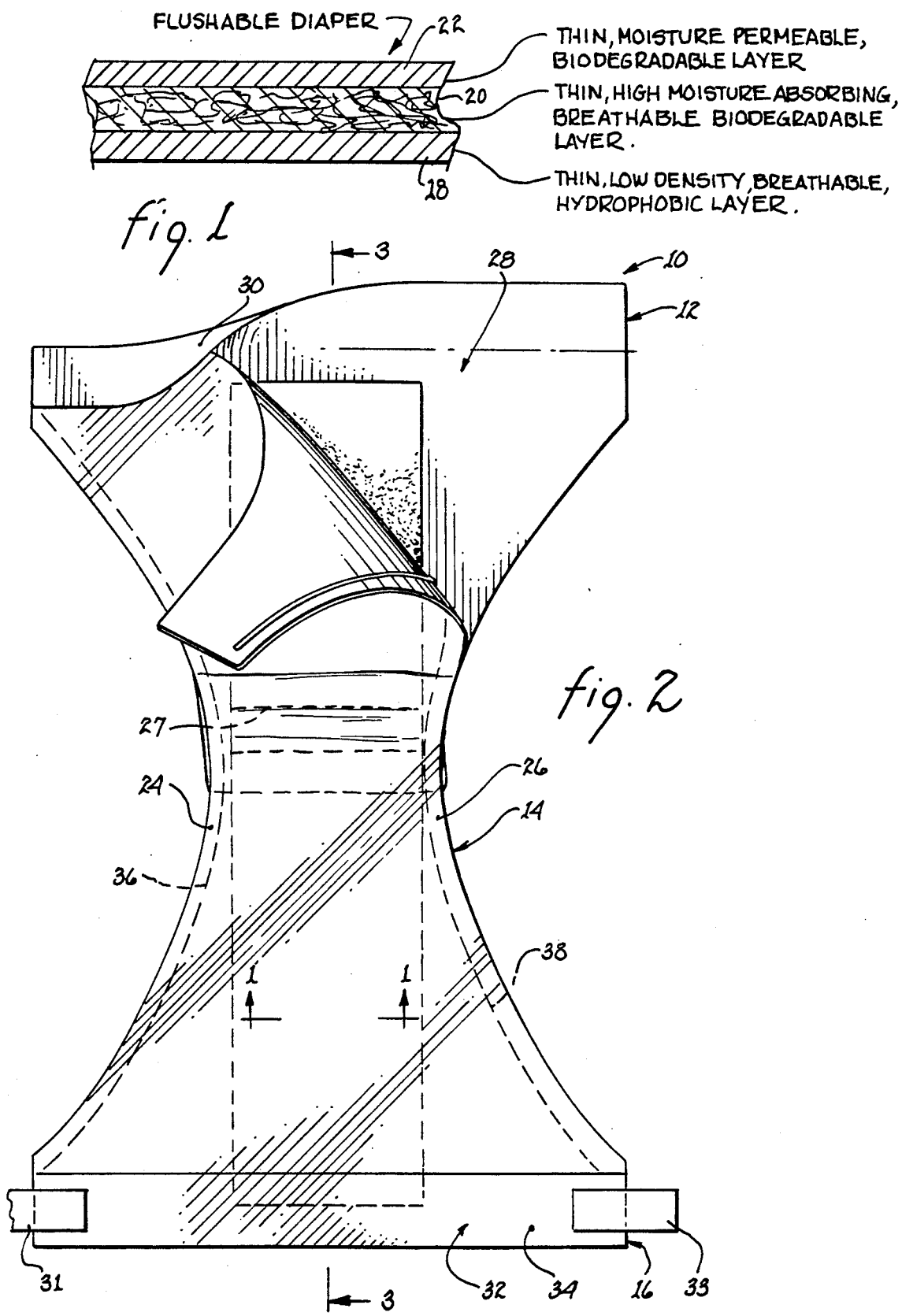

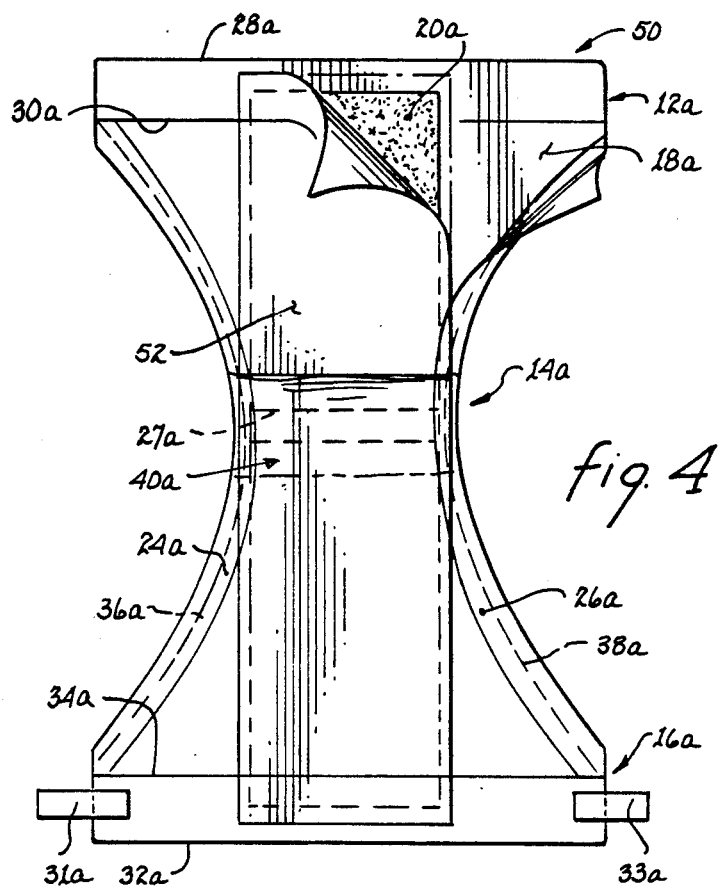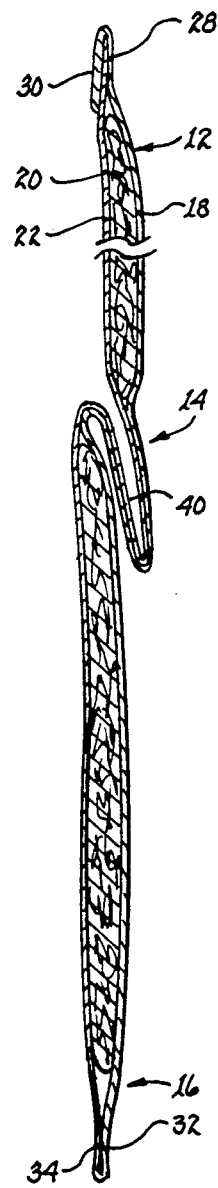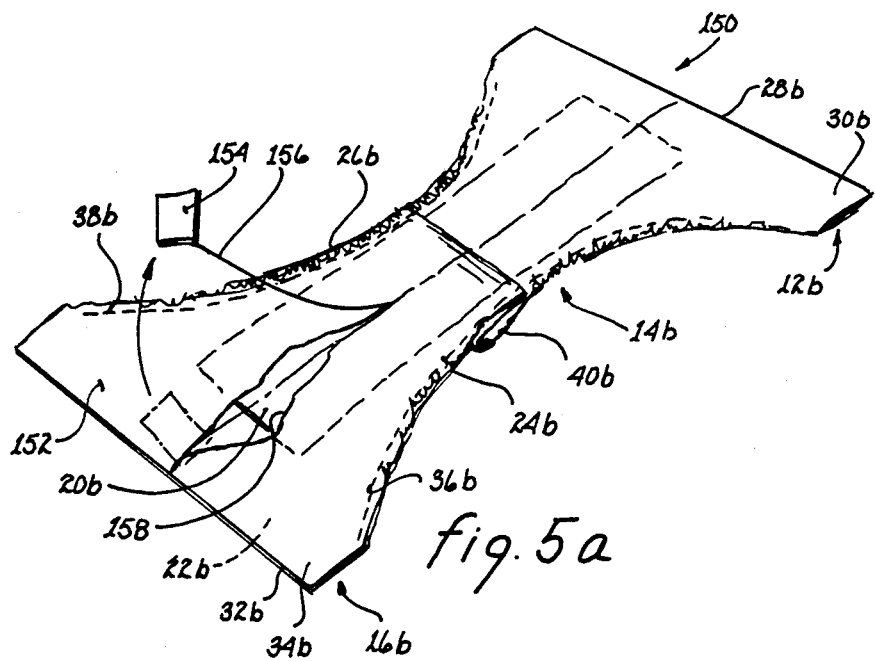

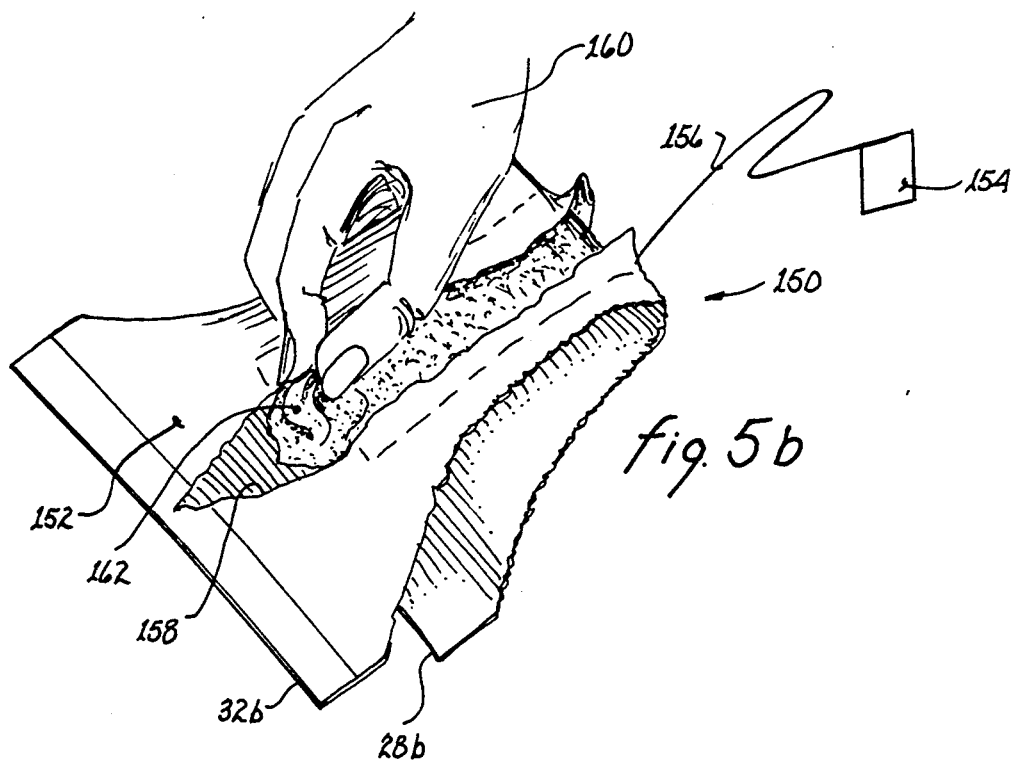
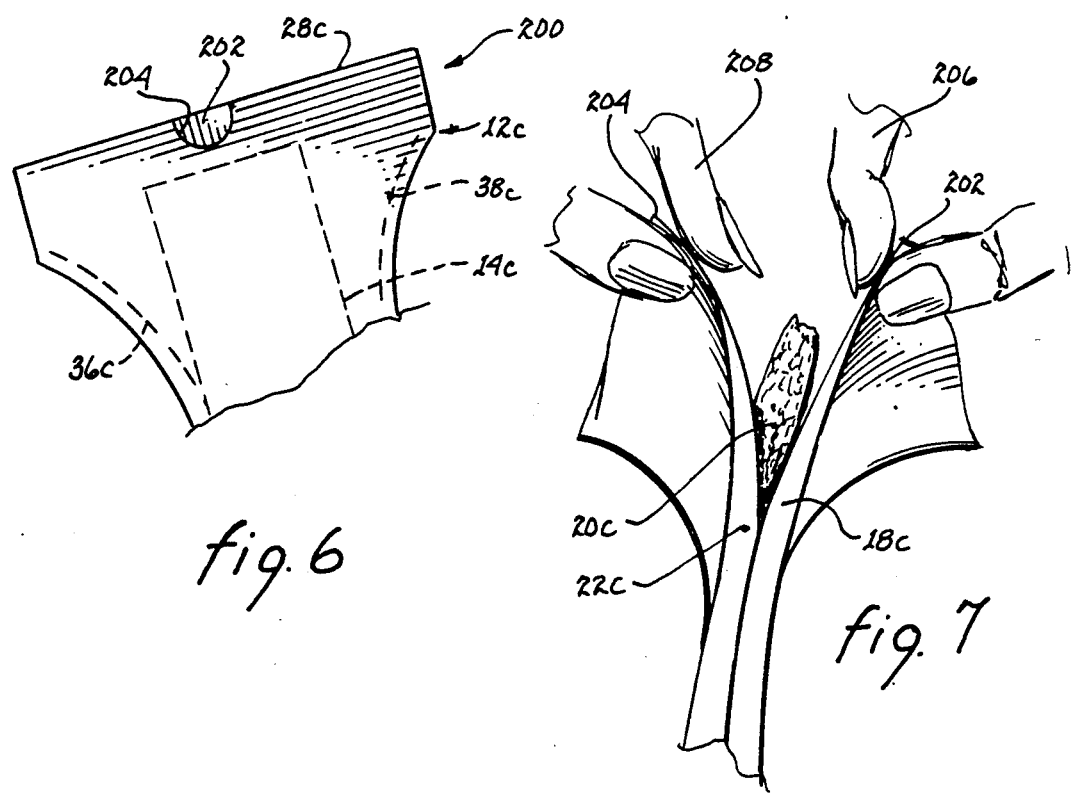

FLUSHABLE DIAPER DEVICE AND METHOD

BACKGROUND OF THE INVENTION

1. Field of Invention

This invention generally relates to a diaper device and method, and, in particular, this invention relates to a totally flushable diaper device and method including having easily flushable portions with quick disassembly means to separate the diaper device into the separate flushable portions which can be flushed down together in one toilet flush.

2. Description of the Prior Art

Prior art types of diapers are described in U.S. Pat. No. 4,643,727, issued Feb. 17, 1987 and in U.S. Pat. No. 4,723,953 issued Feb. 9, 1988.

These prior art diapers include a front portion, a center portion and a rear portion; and are configured as a multi-layer assembly, in section, having a bottom exterior plastic sheet layer, a second wadding batt layer, a third plastic air bubble layer, and a fourth top interior cellulose tissue layer.

One problem with these and other prior art types of diapers is the difficulty of flushing the diaper down a conventional toilet.

As everyone who has had a child or children knows, disposing of diapers that have been used by a child is a necessary and somewhat burdensome chore.

In the past, before the introduction and use of paper type diapers, cloth diapers made of fabric material such as cotton were used which required the constant transportation of these types of diapers because of the need to clean them and to re-use these fairly expensive types of diapers.

Then, fortunately, with the introduction of disposable paper type diapers, parents could merely throw away these paper disposable diapers, after use, thereby avoiding the ammonia and other types of bad odors that were generated by carrying around used wet or soiled diapers.

However, even with the great advance and advantages of disposable paper diapers over the prior cloth type diapers there was still a problem associated with even disposing of the disposable paper diapers. For one thing, disposing of these used, disposable paper diapers in a trash container in a person's home still left the bad odor in the home until the trash container was emptied out outside of the home. Furthermore, if the trash container somehow became wet or soiled because of the used disposable paper diapers, the bad odor remained for a period of time until the trash container was washed or cleaned.

Even dumping the disposable paper diapers outside in a large garbage type can or container could cause the garbage can or container to carry the bad odors and produce a bad smell. Thus, disposing of even the relatively easy to dispose of paper diapers are still somewhat of a problem not including the time lost in transporting the soiled paper diapers to a place where they can be forever disposed of such as in an outside garbage can or container.

Thus, a need existed to provide a flushable diaper device and method that could be quickly and permanently disposed of by flushing a used paper diaper down any conventional toilet.

SUMMARY OF THE INVENTION

Accordingly, it is an object of this invention to provide a flushable diaper device and method.

It is another object of this invention to provide a flushable diaper device and method which permits flushing of the diaper down any conventional toilet.

It is a further object of this invention to provide a flushable diaper device and method which uses a diaper that is very small and easy to flush down a conventional toilet.

It is still another object to this invention to provide a flushable diaper device and method which uses a lightweight, very small diaper similar to a skimpy bikini bottom thereby making it easy to flush down a conventional toilet.

It is a still further object of this invention to provide a flushable diaper device and method which uses a diaper that can be easily separated into plural parts to facilitate flushing down a conventional toilet.

It is another object of this invention to provide a flushable diaper device and method which uses a diaper that is not only flushable down a conventional toilet, but is also entirely or substantially entirely biodegradable for ecology purposes.

BRIEF DESCRIPTION OF THE EMBODIMENTS

In a very brief summary, a flushable diaper is provided. The diaper comprises a front portion, a center portion and a rear portion. The flushable diaper being a multi-layer construction, in section, having a bottom exterior plastic layer, a second middle wadding batt layer and a third top exterior thin layer. The flushable diaper having quick disassembly or separation means for ease of separation of the middle layer from the top and bottom layers or for separation of the top and bottom layers thereby permitting release of or separation of the middle layer. By using the three layer construction and by using the quick disassembly or separation means, the problem of the difficulty of flushing the diaper down even a small toilet is avoided.

In accordance with one embodiment of this invention a flushable diaper is provided comprising, in combination, a three layered combined structure configured as a lightweight, small bikini bottom. The top layer of the three layered combined structure having a thickness of about 1 mil. The middle layer of the three layered combined structure having a thickness of several mils. The bottom layer of the three layered combined structure having a thickness of about 1 mil. Preferably the bottom layer is made of a breathable, hydrophobic material of the kind sold by DuPont under the trademark "EVLON," which consists of 40 percent polyester fiber and 60 percent calcium carbonate. The middle layer comprises a wood pulp type material in order to be capable of absorbing a relatively large amount of liquid waste. The top layer is a material selected from at least one of the group consisting of cotton and rayon in order to provide a thin moisture permeable, biodegradable layer.

In accordance with another embodiment of this invention, a flushable diaper is provided comprising, in combination, a three layered combined structure configured as a lightweight, small bikini bottom. The top layer of the three layered combined structure is made of a thin, moisture permeable, biodegradable material. The middle layer of the three layered combined structure is made of a thin, high moisture absorbing, breathable biodegradable material. The bottom layer of the three layered combination is made of a thin, low density, breathable hydrophobic layer. Thus, the flushable diaper is not only flushable, but substantially biodegradable thereby providing an enhanced diaper product for ecology purposes.

In accordance with a further embodiment of this invention, a flushable diaper is provided comprising, in combination, a thin, lightweight multi-layered combined structure. Separation means coupled to the diaper are provided for permitting the diaper to be manually separated apart to permit the separated portions of the diaper to be flushed together down a toilet in a single flush. In one example, the separation means are located on the back of the diaper. The separation means, in one example, is a draw string substantially centrally disposed on the back of the diaper along the length of the diaper. In another example, the separation means comprises finger griping means located on a perimeter portion of the back of the diaper for permitting separation of at least two layers of the multi-layered combined structure to permit each of the separated layers to be flushed together down a toilet in a single flush.

In accordance with a still further embodiment of this invention, a method is disclosed for providing a flushable diaper comprising the steps of: providing a three layered combined structure configured as a lightweight, small bikini bottom; providing the top layer of the three layered combined structure with a thickness of about 1 mil; providing the middle layer of the three layered combined structure with a thickness of several mils; and providing the bottom layer of the three layered combined structure with a thickness of about 1 mil.

In accordance with another embodiment of this invention a method is disclosed for providing a flushable diaper comprising the steps of: providing a three layered combined structure configured as a lightweight, small bikini bottom; providing the top layer of the three layered combined structure made of a thin, moisture permeable, biodegradable material; providing the middle layer of the three layered combined structure made of a thin, high moisture absorbing, breathable biodegradable material; and providing the bottom layer of the three layered combination made of a thin, low density, breathable hydrophobic layer.

The foregoing and other objects, features and advantages will be apparent from the following description of the preferred embodiment of the invention as illustrated in the accompanying drawings.

BRIEF DESCRIPTION OF THE DRAWINGS

FIG. 1 is a section view taken along line 1—1 of FIG. 2 which illustrates a diaper according to the invention;

FIG. 2 is the plan view of the diaper according to the invention;

FIG. 3 is a section view as taken along line 3—3 of FIG. 2;

FIG. 4 is a plan view of a second embodiment of a diaper according to the invention;

FIG. 5a is a perspective view of a third embodiment of a diaper according to the invention;

FIG. 5b is a perspective view of the third embodiment of FIG. 5a during one way of disassembly thereof;

FIG. 6 is a partial plan view of a fourth embodiment of a diaper according to the invention; and FIG. 7 is perspective view of the fourth embodiment of the diaper of FIG. 6 during disassembly or separation of the layers thereof.

DESCRIPTION OF THE PREFERRED EMBODIMENT

As shown in FIGS. 1 and 2, a flushable lightweight diaper or assembly 10 is provided for use for a relatively large sized baby or toddler or person diapers are sometimes used for older people or others who cannot control disposing of their wastes. It should be readily understood that the diaper 10 can be made much smaller for tiny infants or somewhat smaller for infants who are several months older. Diaper 10 includes a top portion 12, a center portion 14, which is narrower in plan view than the top portion 12, and a bottom portion 16. Diaper 10 has a substantially hour glass shape, however, the top portion 12 is configured to be placed over the buttocks of the infant, baby, toddler or person using the diaper 10. Preferably, the distance from the center of the center portion 14 to the end of the top portion 12 is longer than the distance from the center of the center portion 14 to the end of bottom portion 16.

As shown in FIG. 1, in section view, diaper 10 has a bottom exterior layer 18, a middle layer 20, which has a rectangular shape in plan view and which is preferably narrower in plan view than the bottom exterior layer 18, and a top interior layer 22, which is preferably (in the embodiment of FIG. 2) about the same size and shape as the bottom exterior layer 18 (see FIG. 2).

Center portion 14 has a left side edge portion 24, which has a curved concave shape, and has a right side edge portion 26, which also has a curved concave shape. The center portion 14 has an overlay area 27 which separates the middle layer 20 (see FIG. 1) into two rectangular pieces thereby providing an expansion area for different size uses.

Top portion 12 has an edge portion 28, which has a single-fold extension portion 30, that is used to permit the top layer 22 to be bonded in place with respect to the bottom layer 18 by means such as a heat press or by adhesive means.

Bottom portion 16 has an edge portion 32, which has a similar, bonded, rear, single-fold extension portion 34. The edge portion 32 preferably has adhesive strips 31, 33 for use in permitting the diaper 10 to be tightened about the lower portion of a person's torso for use.

Left and right edges 24, 26 preferably have respective, shortened, elastic strings 36, 38, which provide a crimped elongate type of edge. Strings 36, 38 are preferably sewn through adjacent portions of bottom layer 18 and top layer 22.

As shown in FIG. 3, in section view, center portion 14 preferably has a double-fold portion 40, which can lengthen or shorten when stretched, to suit babies toddlers or person's of different sizes.

Materials used are indicated hereafter. Bottom exterior layer 18 is a material, which is sold under the trademark "EVLON" by the DuPont Company. This material of bottom layer 18, which is about 1.2 mils in thickness, is a microporous barrier film, which has a low rustle for quietness and which is like a textile for softness to the hands and skin and which is breathable for comfort and healthcare. Bottom layer 18 is a thin, low density, breathable substantially degradable layer and a hydrophobic layer to protect against any leakage of water from the moisture absorbing middle layer 20.

Middle layer 20 is made of a conventional diaper material that is used for absorbing moisture or liquid waste, which is a wood pulp, water absorbing, material, and which is preferably several mils in thickness. Middle layer 20 is a thin, high moisture absorbing, breathable, biodegradable layer.

Top interior layer 22 is preferably made of a cotton or rayon material, which is preferably about 1 mil in thickness. The layer 22 is a thin, moisture permeable, biodegradable layer. Preferably, the diaper 10 is configured to not only be thin and thus light in weight, but the overall dimensions thereof are a bikini bottom type configuration thereby further enhancing the flushability of the diaper 10, after use, in any toilet in a single flush. Also, the distance from the center of the center portion 14 to the edge of the top portion 12 is substantially longer than the distance from the center portion 14 to the edge of the bottom portion 16 thereby, with the overall combined layer configuration of the top portion 12, permitting the top portion 12 to adequately serve to take care of containing all a person's wastes.

As shown in FIG. 4, a second embodiment of a flushable diaper 50 is illustrated. Parts of the second flushable diaper embodiment 50, which are the same as corresponding parts of the first embodiment flushable diaper 10, have the same materials but with a subscript "a" added thereto. Diaper 50 has a top portion 12a and a center portion 14a and a bottom portion 16a. Diaper 50, in section, has a bottom exterior layer 18a and a middle layer 20a, and a top interior layer 52. Middle layer 20a has a rectangular shape and is narrower than bottom layer 18a like the corresponding elements shown in FIGS. 1 and 2. Top layer 52 also has a rectangular shape, and is narrower than bottom layer 18a and is slightly wider than middle layer 20a. Top layer 52 is bonded along its edges to bottom layer 18a. Thus, in this embodiment, there is a saving in cost (less material is needed for top layer 52 then for the corresponding top layer 22 FIGS. 1 and 2), weight and in density thereby further enhancing the flushability of the diaper 50.

Center portion 14a has a left side, concave, edge portion 24a, and has a right side, concave, edge portion 26a. Middle layer 20a has a cutout area 27a, which separates middle layer 27a into two pieces.

Top portion 12a has a front edge portion 28a, which has a front, single-fold extension portion 30a. Bottom portion 16a has a back edge portion 32a, which has a back single-fold extension portion 34a, and adhesive tabs 31a, 33a for use in attaching the diaper 50 around the bottom portion of a person's torso.

Left concave edge 24a and right concave edge 26a have respectively a shortened elastic left string 36a and right string 38a, which cause each of these concave edges to have a crimped, elongate type of edge. Strings 36a, 38a are preferably sewn through a series of points along respective concave edges 24a, 26a of bottom layer 18a.

Center portion 14a has a double-fold portion 40a which lengthens or shortens to suit the size of the baby or person that uses the diaper 50.

The materials of layers 18a, 20a, 52 are the same as the materials of respective layers 18, 20, 22 of the first embodiment diaper 10.

As shown in FIGS. 5a and 5b, a third embodiment diaper 150 is provided. The parts of the third embodiment diaper 150 which are the same as the parts of the first embodiment diaper 10 have the same numerals, but with a subscript "b" added thereto. Diaper 150 has a top portion 12b, a center portion 14b and a bottom portion 16b. Diaper 150, in section, has a bottom exterior layer 152, a middle layer 20b and a top interior layer 22b. In FIG. 5a, diaper 150 is shown in an upside-down position for ease of illustration of bottom layer 152. Middle layer 20b has a rectangular shape and is narrower than bottom layer 152. Top layer 22b has preferably in this embodiment, the same size, shape and configuration as bottom layer 152. In an alternate design, top layer 22b can be a rectangular shape, which can be narrower than bottom layer 152 as shown in the embodiment of FIG. 4. Center portion 14b has a left side concave, edge portion 26b.

Top portion 12b has a front edge portion 28b, which has a front single-fold extension portion 30b. Bottom portion 16b has a back edge portion 32b, which has a back single-fold extension portion 34b and adhesive tabs (not shown).

Left concave edge 24b and right concave edge 26b have respectively a left elastic string 36b and a right elastic string 38b. Center portion 14b has a double-fold portion 40b.

Bottom layer 152 has a tab 154 and, elongate tear string 156. By pulling tab 154, string 156 tears, rips or tears apart bottom layer 152 forming ripped edges 158, 159. Thus, the bottom layer 152 can be manually separated apart and, since the middle layer 20b is merely made of relatively thin, wood pulp material and the top layer 22b is made of a think cotton or rayon material, the entire diaper 150 can be separated in two parts, after use, thereby providing two parts that can be easily flushed down a toilet in one flush. As shown in FIG. 5b, a person's hand 160 can be used, but only if absolutely necessary, to pull out a loose portion 162 of the middle layer 20b between the edges 158, 159. Thus, the separated the parts of the diaper 150 can then be together flushed down any toilet.

As shown in FIGS. 6 and 7, a fourth embodiment diaper 200 is provided. Parts of the fourth embodiment diaper 200 which are the same as corresponding parts of the first embodiment diaper 10 have the same materials, but with a subscript "c" added thereto.

Diaper 200 has a top portion 12c, a center portion 14c and a bottom portion (not shown). As shown in FIG. 7, diaper 200, in section, has a bottom exterior layer 18c, and a middle layer 20c and a top interior layer 22c. Top portion 12c has a front edge portion 28c. At front edge portion 28c, top layer 22c and bottom layer 18c are preferably joined by a heated pressure operation or by a suitable adhesive or the like, which is easily opened by opposite forces acting in opposite directions and which act normal to the surface of edge 28c.

Preferably at the center of edge 28c, bottom layer 18c has a semicircular tab bonded thereto, and top layer 22c has a semicircular opening or cut out for ease of griping portions 204 and 202 (of the bottom layer 18c) for ease of separating layers 18c, 22c by opposite hands 206, 208 thereby separating the diaper 200 into two or three parts for a single flush down a toilet.

By separating layer 18c from layers 20c, 22c, and by separating layer 22c from layers 18c, 20c, there are three separate pieces or parts of diaper 200. These three parts can be flushed down the toilet in a single flush.

The materials of layers 18c, 20c, 22c are the same as the materials of respective layers 18, 20, 22 of the first embodiment diaper 10.

The advantages of the diaper embodiments 10, 50, 150, 200 are indicated hereafter.

(A) The problem of the prior art diaper and the difficulty of flushing the prior art diaper down a small toilet is avoided by each of the embodiments 10, 50, 150, 200.

(B) Each diaper 10, 50, 150, 200 is usable for babies, toddlers, or even adults.

(C) Each diaper 10, 50, 150, 200 is lightweight and configured as a small bikini bottom and is useable for any child or for a fully grown person.

(D) Each diaper 10, 50, 150, 200 is a relatively low density assembly which can be readily flushed down a toilet.

(E) Parts of each diaper 150, 200 can be readily separated; and can be flushed down a toilet in a single flush.

(F) Each of the diapers 10, 50, 150 and 200 is substantially biodegradable for ecology purpose.

While the invention has been described in its preferred embodiment, it is to be understood that the words which have been used are words of description rather than limitation and that changes may be made within the purview of the appended claims without departing from the true scope and spirit of the invention in its broader aspects.

I claim:

1. A flushable diaper comprising, in combination, a three layered combined structure configured as a lightweight, small bikini bottom; the top layer of said three layered combined structure having a thickness of about 1 mil; the middle layer of said three layered combined structure having a thickness of several mils; and the bottom layer of said three layered combined structure having a thickness of about 1 mil, wherein said bottom layer consists of a 40% polyester fiber and 60% calcium carbonate composition available under the trade name "EVLON."

2. The flushable diaper of claim 1 wherein said middle layer comprises a wood pulp type material; and wherein said top layer is a material selected from at least one of the group consisting of cotton and rayon.

3. A flushable diaper comprising, in combination, a three layered combined structure configured as a lightweight, small bikini bottom; wherein the top layer of said three layered combined structure is made of a thin, moisture permeable, biodegradable material; wherein the middle layer of said three layered combined structure is made of a thin, high moisture absorbing, breathable, biodegradable material; and wherein the bottom layer is made of a thin, low density, breathable, hydrophobic material that is a 40% polyester fiber and 60% calcium carbonate composition available under the trade name "EVLON."

4. The flushable diaper of claim 3 wherein said bottom layer is substantially degradable.

5. The flushable diaper of claim 3 wherein said bottom layer is about 1 mil thick.

6. The flushable diaper of claim 3 wherein said bottom layer has a thickness of about 1 mil, said middle layer comprises a wood pulp type material having a thickness of several mils, and said top layer is made of a material selected from at least one of the group consisting of cotton and rayon having a thickness of about 1 mil.

7. A method for providing a flushable diaper comprising the steps of: providing a three layered combined structure configured as a lightweight, small bikini bottom; providing the top layer of said three layered combined structure having a thickness of about 1 mil; providing the middle layer of said three layered combined structure having a thickness of several mils; and providing the bottom layer of said three layered combined structure having a thickness of about 1 mil and consisting of a thin, low density, breathable, hydrophobic material that is a 40% polyester fiber and 60% calcium carbonate composition available under the trade name "EVLON."

8. The method of claim 7 wherein said middle layer comprises a wood pulp type material; and said top layer is a material selected from at least one of the group consisting of cotton and rayon.

9. A method for providing a flushable diaper comprising the steps of: providing a three layered combined structure configured as a lightweight, small bikini bottom; providing the top layer of said three layered combined structure made of a thin, moisture permeable, biodegradable material; providing the middle layer of said three layered combined structure made of a thin, high moisture absorbing, breathable, biodegradable material; and providing the bottom layer of said three layered combined structure having a thin, low density, breathable hydrophobic material that is a 40% polyester fiber and 60% calcium carbonate composition available under the trade name "EVLON."

10. The method of claim 9 wherein said bottom layer is substantially degradable.

11. The method of claim 9 wherein said bottom layer is about 1 mil thick.

12. The method of claim 9 wherein said bottom layer has a thickness of about 1 mil, said middle layer comprises a wood pulp type material having a thickness of several mils, and said top layer is made of a material selected from at least one of the group consisting of cotton and rayon having a thickness of about 1 mil.

13. In a multi-layer diaper preferably for use for infants, at least one layer of said diaper made of a thin, low density, breathable, hydrophobic material made of a 40% polyester fiber and 60% calcium carbonate composition available under the trade name.

* * * * *

UNITED STATES PATENT AND TRADEMARK OFFICE
CERTIFICATE OF CORRECTION

PATENT NO. : 5,026,363

DATED : June 25, 1991

INVENTOR(S) : Darin D. Pratt

It is certified that error appears in the above-identified patent and that said Letters Patent is hereby corrected as shown below:

In Column 8, Claim 13, line 52, after the word "name," please add the word--EVLON--.

Signed and Sealed this

Seventeenth Day of November, 1992

*Attest:*

DOUGLAS B. COMER

*Attesting Officer*   Acting Commissioner of Patents and Trademarks